(12) United States Patent
Chen

(10) Patent No.: US 7,838,721 B2
(45) Date of Patent: Nov. 23, 2010

(54) DISPOSABLE ARTICLES USING HIGH COLUMN AUL SUPERABSORBENTS

(75) Inventor: Dennis Chen, Bowling Green, KY (US)

(73) Assignee: Paragon Trade Brands, LLC, Great Neck, NY (US)

( * ) Notice: Subject to any disclaimer, the term of this patent is extended or adjusted under 35 U.S.C. 154(b) by 1604 days.

(21) Appl. No.: 10/409,605

(22) Filed: Apr. 9, 2003

(65) Prior Publication Data
US 2004/0204696 A1    Oct. 14, 2004

(51) Int. Cl.
*A61F 13/15* (2006.01)
(52) U.S. Cl. .............. 604/367; 604/374; 604/375; 604/378; 604/379; 604/370; 604/385.101
(58) Field of Classification Search .......... 604/378, 604/379, 385.01, 385.101, 380, 382, 383, 604/367, 370, 368, 374, 375
See application file for complete search history.

(56) References Cited

U.S. PATENT DOCUMENTS

| | | | |
|---|---|---|---|
| 5,147,343 A | 9/1992 | Kellenberger | |
| 5,281,207 A | 1/1994 | Chmielewski et al. | |
| 5,425,725 A | 6/1995 | Tanzer et al. | |
| H1565 H | 7/1996 | Brodof et al. | |
| 5,681,300 A | 10/1997 | Ahr et al. | |
| 5,849,002 A | 12/1998 | Carlos et al. | |
| 5,853,402 A | 12/1998 | Faulks et al. | |
| 5,863,288 A | 1/1999 | Baker | |
| 5,882,464 A | 3/1999 | Theisgen et al. | |
| 5,891,120 A | 4/1999 | Chmielewski | |
| 5,922,165 A | 7/1999 | Bitowft et al. | |
| 5,938,650 A | 8/1999 | Baer et al. | |
| 6,068,620 A | 5/2000 | Chmielewski | |

*Primary Examiner*—Jacqueline F. Stephens
(74) *Attorney, Agent, or Firm*—Amster, Rothstein & Ebenstein LLP

(57) ABSTRACT

The present invention relates generally to an absorbent composite for an absorbent article, and more particularly to an absorbent composite comprising fibrous material and superabsorbent material having a Column Absorbency Under Load (CAUL) above 10 g/g. Such an absorbent composite provides a superabsorbent material having superior AUL and permeability, thereby providing improved absorption and rewetting properties. An absorbent article that contains such a composite provides improved ability to absorb and retain fluids, thus preventing excessive rewetting and leakage and making the article more comfortable to wear.

41 Claims, 6 Drawing Sheets

28

28

28

DISPOSABLE ARTICLES USING HIGH COLUMN AUL SUPERABSORBENTS

FIELD OF INVENTION

The present invention relates generally to an absorbent composite, and more particularly to an absorbent garment that contains an absorbent composite, wherein the absorbent composite contains a superabsorbent material having a Column Absorbency Under Load (CAUL) above 10 g/g at 0.3 psi. Such an absorbent composite optimizes AUL and permeability at the same time, thereby providing improved absorption, rewetting and comfort.

BACKGROUND OF THE INVENTION

Disposable absorbent garments such as infant diapers or training pants, adult incontinence products and other such products typically were constructed with a moisture-impervious outer backing sheet, a moisture-pervious body-contacting inner liner sheet, and a moisture-absorbent composite or core sandwiched between the liner and backing sheets. Much effort has been expended to find cost-effective materials for absorbent composites that display favorable liquid absorbency and retention. Superabsorbent materials in the form of granules, beads, fibers, bits of film, globules, etc., have been favored for such purposes. Such superabsorbent materials generally are polymeric gelling materials that are capable of absorbing and retaining even under moderate pressure large quantities of liquid, such as water and body wastes, relative to their own weight.

The superabsorbent material generally is a water-insoluble but water-swellable polymeric substance capable of absorbing water in an amount which is at least ten times the weight of the substance in its dry form. In one type of superabsorbent material, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the superabsorbent polymer (SAP) to be highly hydrophilic. Such modified polymers may also be cross-linked to reduce their water-solubility.

The ability of a superabsorbent material to absorb liquid typically is dependent upon the form, position, and/or manner in which particles of the superabsorbent material are incorporated into the absorbent composite. Whenever a particle of the superabsorbent material and absorbent composite is wetted, it swells and forms a gel. Gel formation can block liquid transmission into the interior of the absorbent composite, a phenomenon called "gel blocking." Gel blocking prevents liquid from rapidly diffusing or wicking past the "blocking" particles (e.g., those particles that have swelled and touched an adjacent swelled particle), causing portions of a partially hydrated core to become inaccessible to multiple doses of urine. Further absorption of liquid by the absorbent core must then take place via a diffusion process. This is typically much slower than the rate at which liquid is applied to the core. Gel blocking often leads to leakage from the absorbent article well before all of the absorbent material in the core is fully saturated.

Despite the incidence of gel blocking, superabsorbent materials are commonly incorporated into absorbent cores because they absorb and retain large quantities of liquid, even under load. However, in order for superabsorbent materials to function, the liquid being absorbed in the absorbent structure must be transported to unsaturated superabsorbent material. In other words, the superabsorbent material must be placed in a position to be contacted by liquid. Furthermore, as the superabsorbent material absorbs the liquid it must be allowed to swell. If the superabsorbent material is prevented from swelling, it will cease absorbing liquids.

Adequate absorbency of liquid by the absorbent core at the point of initial liquid contact and rapid distribution of liquid away from this point is desirable to ensure that the absorbent core has sufficient capacity to absorb subsequently deposited liquids. Previously known absorbent cores have thus attempted to absorb quickly and distribute large quantities of liquids throughout the absorbent core while minimizing gel blocking during absorption of multiple doses of liquid.

In general, some of the important performance attributes of an absorbent core of a diaper (or any other absorbent garment) are functional capacity, rate of absorption, core stability in use, AUL of SAP, ratio of fibrous material to SAP, the type and basis weight of glue or tackifying agent used to adhere the SAP to the fibrous material or tissue wrapping, and the basis weight of the core.

Absorption under load or AUL is a measure of functional capacity and the rate at which that absorption occurs. U.S. Pat. No. 5,147,343, the disclosure of which is incorporated herein by reference in its entirety, discloses that AUL is the ability of a superabsorbent material to swell under an applied force. Specifically, AUL is expressed as the amount (in millimeters) of an aqueous solution (0.9% weight percent sodium chloride) that a superabsorbent material can absorb per gram in one hour under a load of 21,000 dynes per square centimeter. AUL is believed to be a function of both SAP basis weight (mass per unit area) and the composition of SAP used in the composite.

It is known to provide absorbent composites comprised of, for example, upper and lower layers, and a central absorbent layer containing from 50% to 95% by weight SAP. U.S. Pat. No. 6,068,620, the disclosure of which is incorporated herein by reference in its entirety, discloses that the upper and lower layers are preferably comprised of tissue, airlaid fluff pulp or synthetic non-woven fibrous layers. The upper and lower layers are said to assist in maintaining the integrity of the core, the multi-layer layered arrangement is said to minimize gel blocking, and the multi-layer core can be folded in various configurations.

It also is known to provide absorbent cores comprised of differing materials in an attempt to maximize comfort and efficiency of the core, and to provide areas having varying degrees of absorbency. U.S. Pat. No. 5,849,002, the disclosure of which is incorporated by reference herein in its entirety, discloses absorbent cores having three zones: (i) one zone for receiving fluids; (ii) one zone for distributing and storing fluids; and (iii) one zone for preventing leakage. U.S. Pat. No. 5,853,402, the disclosure of which is incorporated by reference herein in its entirety, discloses composite absorbent cores comprising at least an absorbent material and a porous resilient material. Other composite, zoned, or multi-component cores are disclosed in, for example, U.S. Pat. Nos. 5,681,300 (blended absorbent core), 5,882,464 (crimping to join two absorbent structures), 5,891,120 (varying SAP concentration throughout core), 5,425,725 and 5,938,650 (multiple fiber free SAP pockets in core), and 5,922,165 (method of joining outer layers with absorbent core disposed between the outer layers). The respective disclosures of each of these documents are incorporated by reference herein in their entirety.

SUMMARY OF THE INVENTION

It has not heretofore been recognized that AUL and permeability at the same time are important in providing absorbent composites. The importance of these two properties has become increasingly important as absorbent composites contain higher concentrations of SAP and manufacturers look for cost effective ways to deliver effective leakage prevention.

It would be desirable to provide an absorbent composite containing a superabsorbent material having a CAUL above 10 g/g at 0.3 psi in order to provide improved performance. The superior absorption under load and permeability properties of the superabsorbent material improves liquid absorption and retention by the absorbent composite and prevents excessive rewetting and leakage.

It also would be desirable to provide an absorbent garment containing such an absorbent composite. Such an absorbent garment would have an improved ability to absorb and retain fluids and, consequently, prevent excessive rewetting and leakage. This also improves comfort, fit and ease of use for the wearer of the absorbent garment.

It is therefore a feature of an embodiment of the invention to provide an absorbent composite containing a superabsorbent material that has a column absorption under load (CAUL) above 10 g/g at 0.3 psi. An additional feature of the invention is to provide an absorbent composite that provides an improved ability to absorb and retain fluids.

It is an additional feature of an embodiment of the invention to provide an absorbent garment that contains an absorbent composite comprising a superabsorbent material that has a column absorption under load (CAUL) above 10 g/g at 0.3 psi, wherein the absorbent garment has an improved ability to absorb and retain fluids, thereby preventing excessive rewetting and leakage. It is an additional feature of an embodiment of the invention to provide an absorbent garment containing such an absorbent composite that is relatively inexpensive to manufacture, that provides the improved properties above, and that is comfortable to wear.

It is another embodiment of the invention to provide an absorbent garment comprising a top sheet, a back sheet and an absorbent composite disposed between the top sheet and the back sheet, wherein the absorbent composite contains a superabsorbent material that has a column absorption under load (CAUL) above 10 g/g at 0.3 psi. Another feature of an embodiment of the invention is to provide a method of making an absorbent garment that includes providing a top sheet, a back sheet, and an absorbent composite to a garment forming station. The absorbent composite is disposed at least partially between the top sheet an the back sheet at the garment forming station. The absorbent composite contains a superabsorbent material that has a column absorption under load (CAUL) above 10 g/g at 0.3 psi.

These and other features and advantages of the preferred embodiments will become more readily apparent when the detailed description of the preferred embodiments is read in conjunction with the attached drawings.

DETAILED DESCRIPTION OF THE PREFERRED EMBODIMENTS

Figure 1A:
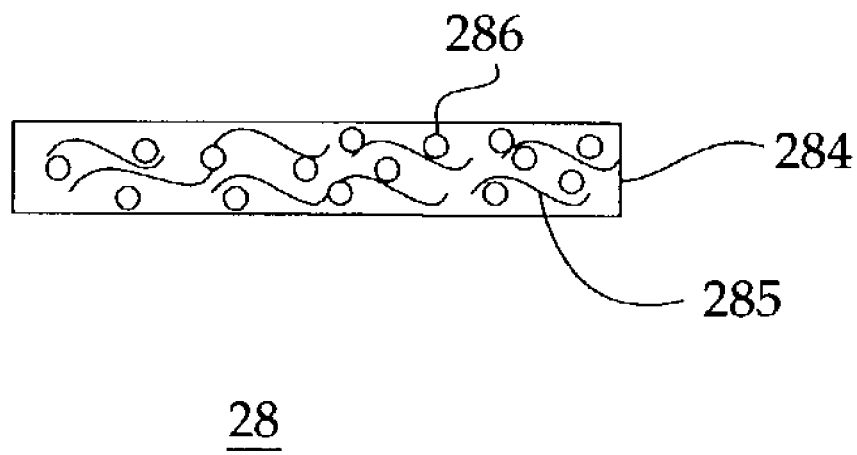
FIG. 1A is a cross-sectional view of an absorbent composite in accordance with one embodiment of the invention; (absorbent layer only)

As used herein, the terms "absorbent garment," "absorbent article" or simply "article" or "garment" refer to devices that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

The present invention may be used with all of the foregoing classes of absorbent garments, without limitation, whether disposable or otherwise. Some of the embodiments described herein provide, as an exemplary structure, a diaper for an infant, however this is not intended to limit the claimed invention. The invention will be understood to encompass, without limitation, all classes and types of absorbent garments, including those described herein. Preferably, the absorbent composite is thin in order to improve the comfort and appearance of a garment.

As used herein and in the appended claims, the singular forms "a," "an," and "the" include plural reference unless the context clearly dictates otherwise. Thus, for example, a reference to "a component" includes a plurality of such components, and a reference to "an absorbent article" is a reference to one or more absorbent articles and equivalents thereof known to those skilled in the art, and so forth.

Throughout this description, the expressions "upper layer," "lower layer," "above" and "below," which refer to the various components included in the absorbent composite and absorbent core embodiments of the invention (including the layers surrounding the absorbent core units) are used merely to describe the spatial relationship between the respective components. The upper layer or component "above" the other component need not always remain vertically above the core or component, and the lower layer or component "below" the other component need not always remain vertically below the core or component. Indeed, embodiments of the invention include various configurations whereby the core is folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, or the like; or a graphic.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the expression "tow fibers" relates in general to any continuous fiber. Tow fibers typically are used in the manufacture of staple fibers, and preferably are comprised of synthetic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow.

Throughout this description, the expression "absorbent composite" relates in general to any composite that contains a superabsorbent material. An "absorbent composite" preferably comprises a mixture of fibrous material and superabsorbent material, and more preferably comprises an upper layer, a lower layer, and an absorbent central layer containing a porous mixture of fibrous material and superabsorbent material disposed between the upper layer and lower layer.

Throughout this description, the expression "outer layers" relates in general to an upper layer and a lower layer in spatial relation to the central absorbent layer, but can include additional layers that may be present. The upper layer and lower layer are preferably made from tissue, however, other materials such as latex or thermally bonded airlaid fluff pulp, (e.g., roll good available from Walkisoft, Merfin or Fort James), or synthetic spunbonded, carded, or hydro-entangled non-woven materials may be used as the upper and lower layers, or may be added as additional layers.

Throughout this description, the expression "absorbent core" relates to an absorbent composite that is used in the manufacture of absorbent garments. Throughout this description, the expression "superabsorbent material" relates generally to a material that can imbibe, absorb or gel about 10 times its own weight of fluid and retain it under moderate pressure, wherein the fluid is taken into the molecular structure and not simply contained in pores from which it could be expressed by squeezing. Throughout this description, the expression "superabsorbent polymer" (SAP) relates generally to a type of superabsorbent material that comprises a polymer.

Throughout this description, the term "permeability" denotes an ability of a superabsorbent material to allow liquid to flow through a pre-swollen gel, and will not gel block the fluid movement. The expression "cross-linking" as it may be used to define certain superabsorbent polymers that may be "cross-linked" is intended to mean any linking that provides stability to the material and makes the superabsorbent material water swellable.

The invention preferably provides an absorbent article containing an absorbent composite having a superabsorbent material with a CAUL above 10 g/g at 0.3 psi. A feature of a preferred embodiment includes a central absorbent layer disposed between an upper layer and lower layer, wherein the central absorbent layer contains a mixture of fibrous material and superabsorbent material throughout its cross-section. The upper and lower layers preferably are made from tissue or any other suitable material so that liquid is absorbed into the central absorbent layer containing the superabsorbent material, wherein the superabsorbent material has a column absorption under load (CAUL) above 10 g/g at 0.3 psi. In this regard, it is preferred that the upper layer, or layer disposed closest to the top sheet, be liquid pervious, and the lower layer, or layer disposed closest to the back sheet, be liquid impervious.

In another embodiment of the invention the absorbent composite contains more than one absorbent layer. The absorbent composite and/or the absorbent garment also may include one or more additional components, such as at least one layer selected from an acquisition layer, a distribution layer, an additional fibrous layer containing superabsorbent material, a wicking layer, a storage layer, or combinations and fragments of these layers. In another embodiment of the invention the absorbent composite has a central absorbent layer without an upper or lower layer.

In another embodiment of the invention the absorbent garment has a front waist region, a rear waist region and a crotch region positioned between the front and rear waist regions. The front waist region and rear waist region can be associated with one another to form a waist opening, and two leg openings. Those skilled in the art recognize that "front" and "rear" in the context of the invention denote for clarity purposes only the front and rear of a user, and that the absorbent article could be reversed whereby the previously described "front" portion becomes the rear portion, and vice versa.

In another embodiment of the invention leg elastics are provided along the leg openings for securely holding the leg openings against the thighs of the wearer to improve containment and fit. A fastening system, either resealable or permanent, preferably holds the absorbent article around the wearer's waist. The fastening system assists in associating the front waist region with the rear waist region. A pair of stand-up leg gathers or waist containment flaps may be attached to or formed from the body's side surface of the top sheet.

The invention now will be described with reference to the attached drawings illustrating preferred embodiments of the invention. For clarity, features that appear in more than one Figure have the same reference number in each Figure.

Figure 1B:
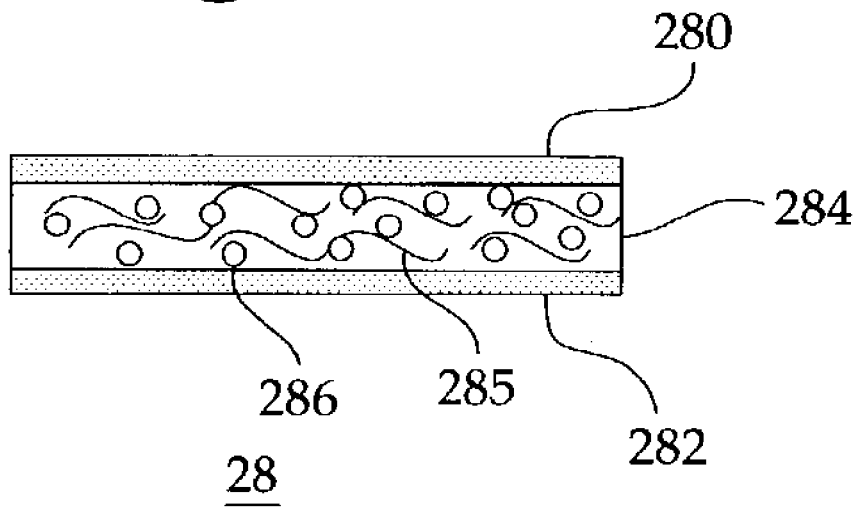
FIG. 1B is a cross-sectional view of an absorbent composite in accordance with another embodiment of the invention; (absorbent layer and outer layers)

FIG. 1A is a cross-section of a preferred embodiment of an absorbent composite 28. An absorbent layer 284 contains a mixture of fibrous material 285 and superabsorbent material 286 throughout the cross-section. FIG. 1B is a cross-section of another preferred embodiment of an absorbent composite 28. A central absorbent layer 284 is disposed between outer layers 280, 282. Outer layer 280 is an upper layer 280 and outer layer 282 is a lower layer. Preferably, upper layer 280 is hydrophilic and fluid pervious, and lower layer 282 is hydrophobic and fluid impervious. It is preferred that upper and lower layers 280, 282 be comprised of a material selected from the group consisting of tissue, airlaid fluff pulp and synthetic non-woven materials. More preferably, upper layer 280 and lower layer 282 are comprised of the same tissue-like material.

The superabsorbent material 286 in the absorbent layer 284 can be present in any concentration, preferably in a concentration of 10% to 95% by weight. The superabsorbent material 286 and fibrous material 285 can be mixed homogenously, arranged in a layered distribution, or mixed heterogeneously so that pockets of superabsorbent material 286 are created. When used in an absorbent garment 10, the absorbent composite 28 can also be called an absorbent core 28. Absorbent composites 28 as disclosed in FIGS. 1A and 1B are customarily used in absorbent garments to absorb and retain bodily excretions that insult the garment.

Figure 2:
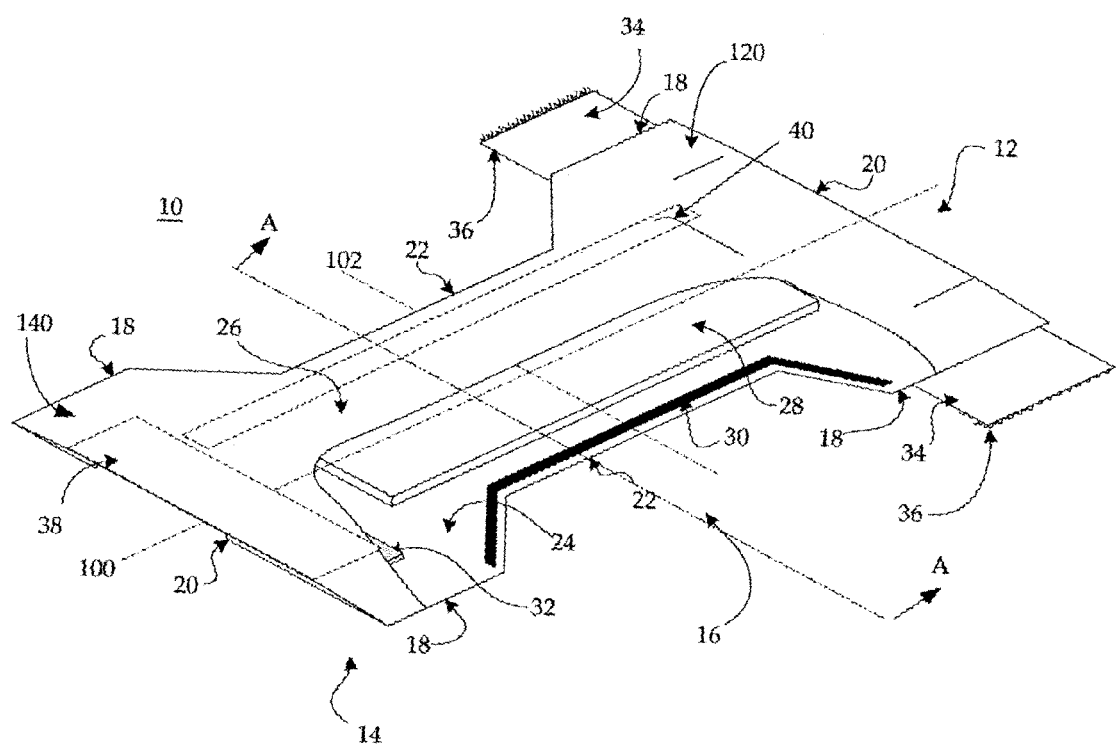
FIG. 2 is a partially cut-away view of an absorbent garment containing an absorbent composite in accordance with one embodiment of the invention.

FIG. 2 is a partially cut away depiction of an exemplary embodiment of an absorbent garment 10 (preferably a disposable absorbent garment) of the present invention. The embodiment shown in FIG. 2 is an infant's diaper, however, this depiction is not intended to limit the invention, and those skilled in the art appreciate that the invention covers other types of absorbent articles. For simplicity, however, the invention will be described with reference to an infant's diaper. The garment 10 of FIG. 2 is depicted in a generally flattened position, with the body-facing side facing down, and with the various elastic components depicted in their relaxed condition with the effects of the elastics removed for clarity (when relaxed, the elastics typically cause the surrounding material to gather or "shirr"). In the flattened position, the garment 10 may have a generally hourglass shaped structure, but it may also have any other shape suitable for the given application, such as a rectangular shape, a trapezoidal shape, a "T" shape, and the like.

As used herein, the longitudinal axis 100 of the garment is the dimension of the garment corresponding to the front-to-rear dimension of the user, and the lateral axis 102 of the garment is the dimension corresponding to the side-to-side dimension of the user.

In use, the invention comprises a pant-like garment 10 having a waist-encircling region and a crotch region. The waist-encircling region may comprise a first waist region 12, disposed adjacent to, for example, the back waist region of a wearer's body, and a second waist region 14, disposed adjacent to, for example, the front waist region of a wearer's body. The first and second waist regions 12, 14, may correspond to the back and front of the wearer's body, respectively, depending on whether garment 10 is attached in front of or behind the subject wearer. The first and second waist regions are joined together at or near their lateral edges 18, causing the longitudinally distal edges 20 of the garment 10 to form the perimeter of a waist opening. A crotch region 16 extends between the first and second waist regions 12, 14, and the crotch edges 22 form the perimeter of a pair of leg openings, when the garment 10 is placed on a subject wearer.

The garment 10 preferably comprises a top sheet 24, and a back sheet 26, which may be substantially coterminous with the top sheet 24. When the garment 10 is being worn, the top sheet 24 faces the wearer's body, and the back sheet 26 faces away from the wearer. An absorbent composite 28 preferably is disposed between at least a portion of the top sheet 24 the back sheet 26.

An embodiment of the present invention may further comprise various additional features. One or more pairs of elastic gathers 30 may extend adjacent the crotch edges 22. The garment 10 may also comprise one or more waste containment systems, such as inboard standing leg gathers 40, which preferably extend from the second waist region 14 to the first waist region 12 along opposite sides of longitudinal center line 100 (only one standing leg gather system 40 is shown in FIG. 1 for purposes of clarity). One or both of the first and second waist regions 12, 14 may also be equipped with strips of elastic waist foam 32 or other elastically extensible material, which help contract the garment around the wearer's waist, providing improved fit and leakage prevention.

The absorbent garment 10 also preferably includes fastening elements to enable attachment of the first waist region 12 to second waist region 14. Fastening elements preferably include a pair of tabs 34 that extend laterally away from opposite lateral edges 18 of the first waist region 12 of the garment 10. The tabs 34 may comprise an elastically extensible material (not shown), and may be designed to stretch around a wearer's waist to provide improved fit, comfort, and leakage protection. Such elasticized tabs 34 may be used in conjunction with, or in lieu of, waist foam 32, or other elastically extensible materials 32.

At least one fastening mechanism 36 (collectively referred to as "fastener 36") is attached to each tab 34 for attaching the tab to the second waist region 14, thereby providing the garment 10 with a pant-like shape, and enabling garment 10 to be fixed or otherwise fitted on the wearer. The fasteners 36 may attach to one or more target devices 38 located in the second waist region 14.

Although not shown in the drawings, the absorbent garment 10 may also include grips attached along one of its edges proximal to each tab 34 to enable a caregiver to pull the grips, and not on the ends of the tabs 34, around the wearer and over the target devices 38 to thereby secure the fasteners 36 to the one or more target devices 38.

The various parts of the garment 10 can be attached to one another or associated with one another to form a structure that preferably maintains its shape during the useful life of the garment 10. As used herein, the terms "attached," "joined," "associated," and similar terms encompass configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the respective parts of the garment 10 to one another.

The top sheet 24 and back sheet 26 may be constructed from a wide variety of materials known in the art. The invention is not intended to be limited to any specific materials for these components. The top sheet 24 and back sheet can be shaped and sized according to the requirements of each of the various types of absorbent garment, or to accommodate various user sizes. In an embodiment of the invention in which the garment 10 is a diaper or an adult incontinence brief, the combination of top sheet 24 and back sheet 26, may have an hourglass shape, as seen in FIG. 1, or may have a rectangular, trapezoidal, "T" shape, or other shape.

Due to the wide variety of backing and liner sheet construction and materials currently available, the invention is not intended to be limited to any specific materials or constructions of these components. The back sheet 26 preferably is made from any suitable pliable liquid-impervious material known in the art. Typical back sheet materials include films of polyethylene, polypropylene, polyester, nylon, and polyvinyl chloride and blends of these materials. For example, the back sheet can be made of a polyethylene film having a thickness in the range of 0.02-0.04 mm. The back sheet 26 may be pigmented with, for example, titanium dioxide, to provide the garment 10 with a pleasing color or to render the back sheet 26 opaque enough that exudates being contained by the garment 10 are not visible from outside the garment. In addition, the back sheet 26 may be formed in such a manner that it is opaque, for example, by using various inert components in the polymeric film and then biaxially stretching the film. Other back sheet materials will be readily apparent to those skilled in the art. The back sheet 26 preferably has sufficient liquid imperviousness to prevent any leakage of fluids. The required level of liquid imperviousness may vary between different locations on the garment 10.

The back sheet 26 may further comprise separate regions having different properties. In a preferred embodiment, portions of the back sheet 26 are air-permeable to improve the breathability, and therefore comfort, of the garment 10. The different regions may be formed by making the back sheet 26 a composite of different sheet materials, chemical treatment, heat treatment, or other processes or methods known in the art. Some regions of the back sheet 26 may be fluid pervious. In one embodiment of the invention, the back sheet 26 is fluid impervious in the crotch 16, but is fluid pervious in portions of the first and second waist regions 12, 14. The back sheet 26 may also be made from a multi-layer of overlaid sheets of material.

The moisture-pervious top sheet 24 can be comprised of any suitable relatively liquid-pervious material known in the art that permits passage of liquid there through. Non-woven liner sheet materials are exemplary because such materials readily allow the passage of liquids to the underlying absorbent composite 28. Examples of suitable liner sheet materials include non-woven spun bond or carded webs of polypropylene, polyethylene, nylon, polyester and blends of these materials.

The back sheet 26 may be covered with a fibrous, non woven fabric such as is disclosed, for example, in U.S. Pat. No. 4,646,362 issued to Heran et al., the disclosure of which is hereby incorporated by reference in its entirety and in a manner consistent with this disclosure. Materials for such a fibrous outer liner include a spun-bonded non woven web of synthetic fibers such as polypropylene, polyethylene or polyester fibers; a non woven web of cellulosic fibers, textile fibers such as rayon fibers, cotton and the like, or a blend of cellulosic and textile fibers; a spun-bonded non woven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers. Alternatively, the back sheet 26 may comprise three panels wherein a central poly back sheet panel is positioned closest to absorbent composite 28 while outboard non-woven breathable side back sheet panels are attached to the side edges of the central poly back sheet panel. Alternatively, the back sheet 26 may be formed from microporous poly coverstock for added breathability.

Figure 3:
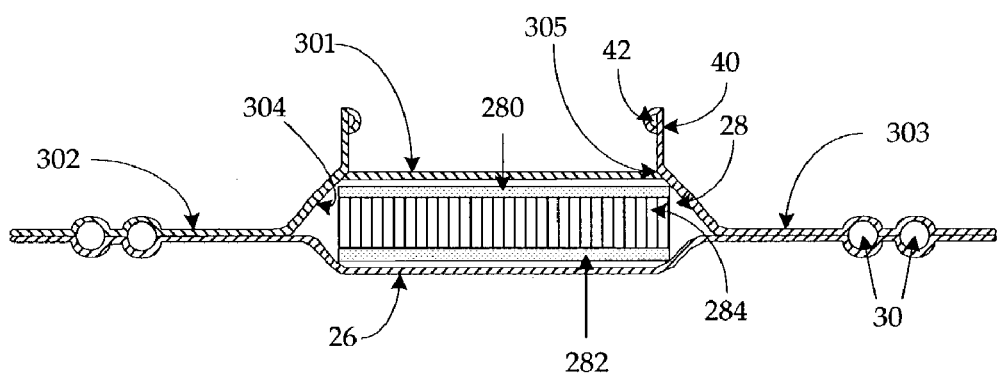
FIG. 3 is a cross-sectional view of the absorbent garment of FIG. 2 taken along line A-A.

As illustrated in more detail in FIG. 3, the top sheet 24 may be formed of three separate portions or panels. Those skilled in the art will recognize, however, that top sheet 24 need not be made of three separate panels, and that it may be comprised of one unitary item. A first central top sheet panel 301 may comprise a central top sheet panel formed from preferably a liquid-pervious material that is either hydrophobic or hydrophilic. The central top sheet panel 301 may be made from any number of materials, including synthetic fibers (e.g., polypropylene or polyester fibers), natural fibers (e.g., wood or cellulose), apertured plastic films, reticulated foams and porous foams to name a few. One preferred material for a central top sheet panel 301 is a cover stock of single ply non-woven material which may be made of carded fibers, either adhesively or thermally bonded, perforated plastic film, spun bonded fibers, or water entangled fibers, which generally weigh from 0.3-0.7 oz./sq. yd. and have appropriate and effective machine direction and cross-machine direction strength suitable for use as a baby diaper cover stock material. The central top sheet 301 panel preferably extends from substantially the second waist region 14 to the first waist region 12, or a portion thereof. The first top sheet panel also may fully envelop the composite 28, such that the second and third top sheet panels 302, 303 are disposed laterally away from the lateral edges of composite 28.

The second and third top sheet panels 302, 303 (e.g., outer top sheet panels), in this alternative embodiment may be positioned laterally outside of the central top sheet panel 301. The outer top sheet panels 302, 303 are preferably substantially liquid-impervious and hydrophobic, preferably at least in the crotch area. The outer edges of the outer top sheet panels may substantially follow the corresponding outer perimeter of the back sheet 26. The material for the outer top sheet portions or panels is preferably polypropylene and can be woven, non-woven, spun bonded, carded or the like, depending on the application.

The inner edges 304 (FIG. 3) of the outer top sheet portions or panels 302, 303 preferably are attached by, e.g., an adhesive, to the outer edges 305 of the inner top sheet portion or panel 301. At the point of connection with the outer edges 305 of the inner top sheet portion or panel 301, the inner edges 304 of the outer top sheet portions or panels 302, 303 extend upwardly to form waste containment flaps 40. The waste containment flaps 40 preferably are formed of the same material as the outer top sheet portions or panels 302,303, as in the embodiment shown. They are preferably an extension of the outer top sheet portions or panels 302, 303.

The waste containment flaps 40 may be treated with a suitable surfactant to modify their hydrophobicity/hydrophilicity as desired, and they may be treated with skin wellness ingredients to reduce skin irritation. Alternatively, the waste containment flaps 40 may be formed as separate elements and then attached to the body side liner. In this alternative embodiment, the central top sheet portion or panel 301 may extend past the connection point with the waste containment flaps 40, and even extend to the periphery of the back sheet 26.

The waste containment flaps 40 preferably include a portion that folds over onto itself to form a small enclosure. At least one, and depending on the size of the enclosure sometimes more than one, elastic member 42 may be secured in the enclosure in a stretched condition. As is well known in the art, when the flap elastic 42 attempts to assume the relaxed, unstretched condition, the waste containment flaps 40 rise above the surface of the central top sheet portion or panel 301.

The top sheet 24 (as well as top sheet portions 301, 302, 303) may be made of any suitable relatively liquid-pervious material currently known in the art or later discovered that permits passage of a liquid there through. Examples of suitable top sheet materials include non woven spun-bonded or carded webs of polypropylene, polyethylene, nylon, polyester and blends of these materials, perforated, apertured, or reticulated films, and the like. Non woven materials are exemplary because such materials readily allow the passage of liquids to the underlying absorbent composite 28. The top sheet 24 preferably comprises a single-ply non woven material that may be made of carded fibers, either adhesively or thermally bonded, spun bonded fibers, or water entangled fibers, which generally weigh from 0.3-0.7 oz./sq. yd. and have appropriate and effective machine direction (longitudinal) and cross-machine (lateral) direction strength suitable for use as a top sheet material for the given application. The present invention is not intended to be limited to any particular material for the top sheet 24, and other top sheet materials will be readily apparent to those skilled in the art.

The top sheet 24 may further comprise several regions having different properties. In one embodiment of the present invention, the laterally distal portions of the top sheet 24, especially those used to make second and third top sheet panels 302, 303, preferably are substantially fluid impervious and hydrophobic, while the remainder of the top sheet 24 (e.g., central top sheet panel 301) is hydrophilic and fluid pervious. Different top sheet properties, such as fluid perviousness and hydrophobicity, may be imparted upon the top sheet 24 by treating the top sheet 24 with adhesives, surfactants, or other chemicals, using a composite of different materials, or by other means. The top sheet 24 may also be made from a multi-layer of overlaid sheets of material. The top sheet 24 also may be treated in specific areas like the crotch region, with skin wellness ingredients such as aloe, vitamin E, and the like.

As noted elsewhere herein, the top sheet 24 and back sheet 26 may be substantially coterminous, or they may have different shapes and sizes. The particular design of the top sheet 24 and back sheet 26 may be dictated by manufacturing considerations, cost considerations, and performance considerations. Preferably, the top sheet 24 is large enough to completely cover the absorbent composite 28, and the back sheet 26 is large enough to prevent leakage from the garment 10. The design of top sheet 24 and back sheet 26 is known in the art, and a skilled artisan will be able to produce an appropriate top sheet 24 and an appropriate back sheet 26 without undue experimentation.

The top sheet 24 and the back sheet 26 may be associated with one another using a variety of methods known in the art. For example, they may be thermally, ultrasonically, or chemically bonded to one another. They also may be joined using lines of hot melt adhesive or mechanical fasteners, such as thread, clips, or staples. In one embodiment, a hydrophilic adhesive, such as Cycloflex as sold by National Starch, a corporation headquartered in Bridgewater, N.J., is used to join the top sheet 24 to the back sheet 26. The particular joining method may be dictated by the types of materials selected for the top sheet 24 and back sheet 26.

As mentioned above, the absorbent garment 10 preferably is provided with leg elastics 30 extending through crotch region 16, adjacent crotch edge 22. The absorbent garment 10 of the invention also preferably is provided with waist elastic material 32 optionally in the first and second waist regions, 12, 14, respectively, to enable and assist in stretching around the wearer. The waist elastics 32 may be similar structures or different to impart similar or different elastic characteristics to the first and second waist regions 12, 14 of the garment. In general, the waist elastics 32 may preferably comprise foam strips positioned at the first and second waist regions 12, 14, respectively. Such foam strips preferably are about ½ to about 1½ inches wide and about 3-6 inches long. The foam strips preferably are positioned between the top sheet portions 24 or panels (301, 302, 303) and the back sheet 26. Alternatively, a plurality of elastic strands may be employed as waist elastics rather than foam strips. The foam strips preferably are comprised of polyurethane, but can be any other suitable material that decreases waist band roll over, reduces leakage over the waist ends of the absorbent garment, and generally improve comfort and fit. The first and optional second waist foam strips 32 preferably are stretched 50-150%, preferably 100% more than their unstretched dimension before being adhesively secured between the back sheet 26 and top sheet 24.

Each edge 22 that forms the leg openings preferably is provided with an adjacent leg elastic containment system 30. In the preferred embodiment, three strands of elastic threads (only two strands are shown in FIG. 3 for purposes of clarity) are positioned to extend adjacent to leg openings between the outer top sheet portions or panels 302, 303 and the back sheet 26. Any suitable elastomeric material exhibiting at least an elongation (defined herein as $(L_S-L_R)/L_R$ where $L_S$ is the stretch length of an elastic element and $L_R$ is retracted length, multiplied by 100 to obtain percent elongation) in the range of 5%-350%, preferably in the range of 200%-300%, can be employed for the leg elastics 30. The leg elastics 30 may be attached to the absorbent article 10 in any of several ways which are known in the art. For example, the leg elastics 30 may be ultrasonically bonded, heat/pressure sealed using a variety of bonding patterns, or glued to the garment 10. Various commercially available materials can be used for the leg elastics 30, such as natural rubber, butyl rubber or other synthetic rubber, urethane, elastomeric materials such as LYCRA (DuPont), GLOSPAN (Globe) or SYSTEM 7000 (Fulflex).

The fastening elements, preferably a fastening system 34 (e.g., tab 34) of the preferred embodiment, is attached to the first waist region 12, and it preferably comprises a tape tab or mechanical fasteners 36. However, any fastening mechanism known in the art will be acceptable. Moreover, the fastening system 34 may include a reinforcement patch below the front waist portion so that the diaper may be checked for soiling without compromising the ability to reuse the fastener. Alternatively, other absorbent article fastening systems are also possible, including safety pins, buttons, and snaps.

As stated previously, the invention has been described in connection with a diaper. The invention, however, is not intended to be limited to application only in diapers. Specifically, the absorbent composites of the preferred embodiments may be readily adapted for use in other absorbent garments besides diapers, including, but not limited to, training pants, feminine hygiene products and adult incontinence products.

The underlying structure beneath the top sheet 24 may include, depending on the diaper construction, various combinations of elements, but in each embodiment, it is contemplated that the absorbent garment 10 will preferably include an absorbent composite 28. In addition, additional layers may be disposed between the top sheet 24 and absorbent composite 28, or between the absorbent composite 28 and back sheet 26. An additional layer also may be included in the absorbent composite 28. The additional layer(s) may include a fluid transfer layer, a fluid handling layer, a storage layer, a wicking layer, a fluid distribution layer, and any other layer(s) known to those having ordinary skill in the art.

Although the absorbent composite 28 depicted in FIG. 3 has a substantially rectangular cross-sectional and plan view shape, other shapes may be used, such as a "T" shape or an hourglass shape. The shape of the absorbent composite 28 may be selected to provide the greatest absorbency with a reduced amount of material. The absorbent composite may be associated with the top sheet 24, back sheet 26, or any other suitable part of the garment 10 by any method known in the art, in order to fix the absorbent composite 28 in place. In addition to the respective layers in the absorbent composite 28, as will be described in greater detail hereinafter, the overall absorbent composite 28 may be enclosed within a tissue wrapping, as shown in FIG. 1B and disclosed in U.S. Pat. No.

6,068,620, the disclosure of which is incorporated by reference herein in its entirety. Skilled artisans are capable of designing and wrapping a suitable absorbent composite 28 of the invention, using the guidelines provided herein.

In a preferred embodiment, the central absorbent layer 284 of absorbent composite 28 comprises super absorbent polymer distributed within a fibrous structure. Central absorbent layers 284 of this type generally are known in the art, and exemplary absorbent cores are described in U.S. Pat. No. 6,068,620 and U.S. Pat. No. 5,281,207, both issued to Chmielewski, and U.S. Pat. No. 5,863,288, issued to Baker, the disclosures of each of which are herein incorporated by reference in their entirety and in a manner consistent with this disclosure.

Certain fibrous and particulate additives preferably are used as constituent elements of the absorbent composite 28 to maintain high SAP efficiencies when the SAP concentration is in the range of about 10-95%, more preferably about 40-90%, and most preferably about 50-85%. Super absorbent polymers of the surface cross-linked variety perform best in these multi-layers. These additives preferably are constituent elements of the central absorbent layer 284, and they may be added to any additional layer(s).

The fibrous component of the central layer 284 of absorbent composite 28 may be any fibrous material now known or later discovered. Suitable fibrous materials include fluff pulp, soft and hard Kraft woods, and the like. The fibrous component preferably is comprised of tow fiber, and most preferably is a crimped tow of cellulose acetate or polyester. Before making the absorbent composite that includes a tow fiber, the tow fiber typically is unwound and opened, and then cut at various lengths to provide a fibrous mass of material. Skilled artisans are aware of techniques available to open tow fibers and form the opened fibers into a fibrous mass.

In addition to the tow material used as the fibrous component in central absorbent layer 284, other fibrous components also may be used. For example, additional tow fibers (different from original tow fiber), or a low-density roll good made in a separate process may be used in central absorbent layer 284. Still further yet, the fibrous component could also be a carded web formed on-line. Optionally, it is advantageous to introduce from about 1-5% of a thermally bondable fiber into the fibrous component of the central absorbent layer 284 for wet strength and core stability in use.

To maintain high SAP concentrations, the concentration of fibrous material in the central layer 284 of the absorbent composite 28 of the invention preferably is about 5-90%, more preferably about 10-60%, and most preferably about 15-50%. Most preferably, the central absorbent layer 284 comprises from about 75-85% SAP and from about 15-25% fibrous materials selected from the foregoing group, or the following fibrous components discussed below.

Particulate additives may be added to central absorbent layer 284 in addition to or as a substitute for the foregoing fibrous additives in order to maintain high SAP efficiency. The particulate additives preferably are insoluble, hydrophilic polymers with particle diameters of 100 μm or less. The particulate additives are chosen to impart optimal separation of the SAP particles. Examples of preferred particulate additive materials include, but are not limited to, potato, corn, wheat, and rice starches. Partially cooked or chemically modified (i.e., modifying hydrophobicity, hydrophilicity, softness, and hardness) starches can also be effective. Most preferably, the particulate additives comprise partially cooked corn or wheat starch because in this state, the corn or wheat are rendered larger than uncooked starch and even in the cooked state remain harder than even swollen SAP. In any event, regardless of the particulate additive chosen, one of the many important criteria is to use particulate additives that are hard hydrophilic materials relative to swollen SAP or which are organic or inorganic polymeric materials about 100 microns in diameter. Fibrous and particulate additives can be used together in these absorbent multi-layers. Examples of SAP/particulate and SAP/fiber/particulate additives include those described in, for example, U.S. Pat. No. 6,068,620.

Any superabsorbent polymer (SAP) now known or later discovered may be used in central absorbent layer 284 so long as it is capable of absorbing liquid and so long as it has a CAUL above 10 g/g at 0.3 psi. Useful SAP materials are those that generally are water-insoluble but water-swellable polymeric substance capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility. Examples of suitable SAP are water swellable polymers of water soluble acrylic or vinyl monomers crosslinked with a polyfunctional reactant. Also included are starch modified polyacrylic acids and hydrolyzed polyacrylonitrile and their alkali metal salts.

In accordance with the present invention, the central absorbent layer 284 may be based upon a tow fiber, and preferably, a continuous crimped filament tow. This fiber structure has high structural integrity, and as such, is distinct from a matrix of discontinuous fibers described as fluff, or fluff pulp in the prior art. The high structural integrity enables the production of stronger webs than those formed from discontinuous fibers, which in turn are believed to enable the production of thinner absorbent pads that contain the same or more SAP then conventional "thicker" pads. The invention is not limited, however, to thin absorbent composites, or to absorbent composites employing tow fibers.

The tow fiber can be any continuous or discontinuous thermoplastic filament tow fiber that is capable of being opened and used in combination with SAP in an absorbent core. Preferably, cellulose ester tow is used as the fibrous material in central absorbent layer 284. Non-limiting examples of suitable cellulose esters include cellulose acetate, cellulose propionate, cellulose butyrate, cellulose caproate, cellulose caprylate, cellulose stearate, highly acetylated derivatives thereof such as cellulose diacetate, cellulose triacetate and cellulose tricaproate, and mixtures thereof such as cellulose acetate butyrate. A suitable cellulose ester will include the ability to absorb moisture, preferably is biodegradable, and is influenced not only by the substituent groups but also by the degree of substitution. The relationship between substituent groups, degree of substitution and biodegradability is discussed in W. G. Glasser et al, BIOTECHNOLOGY PROGRESS, vol. 10, pp. 214-219 (1994), the disclosure of which is incorporated herein by reference in its entirety.

Continuous filament tow useful in the present invention is beneficially moisture-absorbent and biodegradable. Accordingly, cellulose acetate tow is typically preferred for use in the invention. Typically, the denier per fiber (dpf) of the tow fiber will be in the range of about 1 to 9, preferably about 3 to 6. For the same weight product, filaments of lower dpf may provide increased surface area and increased moisture absorption. Total denier may vary within the range of about 20,000 to 60,000, depending upon the process used.

It is particularly preferred in the invention to use tow having crimped filaments. Tow materials having crimped filaments are typically easier to open. Separation of filaments resulting from bloom advantageously results in increased available filament surface area for superabsorbent material immobilization and increased moisture absorption. Gel blocking also may be reduced by using crimped tow in the central absorbent layer 284. As therefore may be understood, more crimp is typically better, with in excess of about 20 crimps per inch being usually preferred. Continuous filament, cellulose ester tow having crimped filaments with about 25 to 40 crimps per inch, is commercially available from Hoechst Celanese Corporation, Charlotte, N.C.

If desired, a superabsorbent, absorptive pad of multiple layer thickness, may be provided. To this end, the tow may be, for example, lapped or crosslapped in accordance with conventional procedures. In this way, a superabsorbent, absorptive material of a desired weight and/or thickness may be provided. The specific weight or thickness will depend upon factors including the particular end use. It is especially preferred that the crimped cellulose acetate tow material be opened and then mixed with the SAP particles to form the central absorbent layer 284.

The SAP may be provided in any particle size, and suitable particle sizes vary greatly depending on the ultimate properties desired. Preferably, a fine particulate rather than a coarse particulate, is used in the invention, a SAP having a particle size within the range of from about 100 to about 1,000 µm is used in the invention.

The total basis weights of the absorbent composite 28 including fibrous materials, SAP, tissue, additional layers, and additives, are anywhere from about 100-600 grams per square meter. The most preferred total basis weight of the absorbent composite 28 is from about 250 to about 350 grams per square meter. Optionally, about 1-10%, preferably about 5%, by weight of thermally bondable synthetic fibers can be added to the absorbent composite 28 to impart additional wet strength to the composite. This will improve the stability of the core during use of the diaper. The preferred synthetic fibers are polyolefin/polyester fibers and polyester/polyester bicomponent fibers.

Depending on whether a wet or dry process is used to make the absorbent composite 28, bonding central absorbent layer 284 with any additional layer(s), and tissue layers 280, 282, can be achieved with hydrogen or adhesive bonds. If the material used to form the absorbent composite 28 contains about 1-5% by weight thermally bondable synthetic fibers, bonding can be achieved with thermal bonds.

FIGS. 1A and 1B represent only two possible configuration of absorbent composite 28. In addition to other configurations, additional layers may be present in the absorbent composite. For example, absorbent composite 28 may include an additional layer, and/or an additional layer can be disposed outside absorbent composite 28. Any additional layer can be used, including any layer selected from a fluid acquisition layer, a distribution layer, an additional fibrous layer optionally containing SAP, a wicking layer, a storage layer, or combinations and fragments of these layers. Such layers may be provided to assist with transferring fluids to the absorbent composite 28, handling fluid surges, preventing rewet, containing absorbent material, improving core stability, or for other purposes. For example, a wicking layer having enhanced lateral wicking capabilities may be provided above the absorbent composite shown in FIG. 3, which has enhanced absorbency near its lateral edges. Skilled artisans are familiar with the various additional layers that may be included in an absorbent article, and the present invention is not intended on being limited to any particular type of materials used for those layers. Rather, the invention encompasses all types of wicking layers, all types of distribution layers, etc., to the extent that type of layer is utilized. Furthermore, any of the these additional layers described herein can be used as upper layer 280 and lower layer 282.

It is possible in the present invention that the absorbent composite 28 be folded as it is disposed between the top sheet 24 and back sheet 26. The absorbent composite 28 can be folded in any suitable manner, including any and all of those disclosed in U.S. Pat. No. 6,068,620. Suitable folds include "C" folds, "G" folds, "U" folds, "A" folds, pleats or "W" folds, and the like.

The invention also relates to a method of making an absorbent composite, and an absorbent article that includes providing a top sheet material 24 and a back sheet material 26. The method also includes preparing an absorbent composite 28 by disposing a central absorbent layer comprising a mixture of tow fibers and SAP between an upper layer 280 and a lower layer 282. The method includes disposing the absorbent composite 28 between the top sheet 24 and the back sheet 26.

Figure 4:
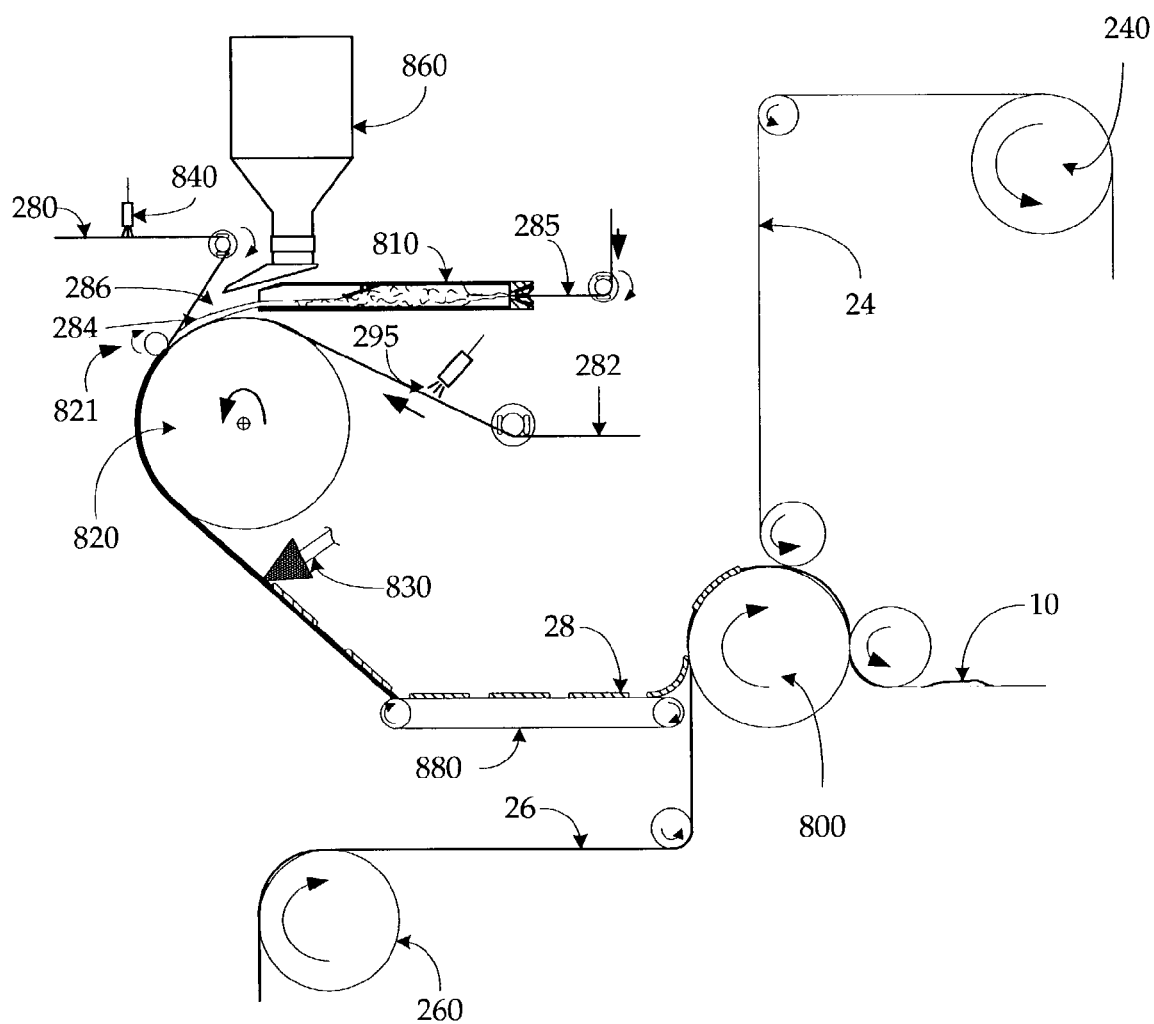
FIG. 4 is an illustration of an apparatus useful in carrying out a method of making an absorbent garment in accordance with the present invention.

FIG. 4 illustrates an apparatus useful in forming an absorbent article 10 in accordance with the present invention. FIG. 4 illustrates preparing an absorbent composite using tow fibers. Skilled artisans recognize that other fibrous materials can be used to make absorbent composite 28, and can modify the method and apparatus of FIG. 4, specifically composite forming station 820, to account for the various types of fibrous material contemplated in the present invention.

Any type of fibrous material 285, and as shown in FIG. 4, any type of tow fiber 285 can be supplied to the apparatus. As conventional in the art, the tow fiber 285 typically is opened prior to forming a fibrous matrix. In this regard, the apparatus includes a tow opener and feeder 810 that is capable of opening any suitable tow material, expanding the tow fiber and feeding the tow fiber to the composite forming station 820. Any suitable tow opener and feeder 810 can be used in the method of the invention.

The tow fibers 285 preferably are mixed with superabsorbent polymer (SAP) material 286 to form central absorbent layer 284. The SAP is fed to the core forming station 820 by any SAP feeder 860 capable of feeding the SAP to the core forming station 820. Those skilled in the art are capable of designing a suitable SAP feeder 860 and nozzle configuration to provide adequate mixing of SAP material 286 and tow fibers 285 to form central absorbent layer 284.

The absorbent composite 28 can be formed at composite forming station 820, where central absorbent layer 284, comprised of SAP material 286 and tow fibers 285, is disposed between an upper layer 280, and a lower layer 282. Upper and lower layers 280, 282 can be fed to composite forming unit 820 using any supplying mechanism known in the art, and preferably are fed through one or more feed rollers. Adhesive 295 can be applied to either upper layer 280 or lower layer 282, to both layers, or to neither layer, by an adhesive applicator 840. Again, any mechanism capable of supplying an adhesive, albeit a spray adhesive, or one that is "rubbed" on, can be used in the invention. Suitable adhesives 295 include any adhesive commonly employed in absorbent garments that is useful in adhering one or more tissue and/or non-woven materials together. It is particularly preferred to use construction adhesives, including HL-1258 by H. B. Fuller Company of St. Paul, Minn.; Findley 2031 and H2587-01 by Ato Findley Inc. of Wauwatosa, Wis.; and NS34-5665 by National Starch Co. of Bridgewater, N.J. Other adhesives that may be used in the invention include 34-578A, available from National Starch Co. of Bridgewater, N.J. Any of these adhesives may be used in all adhesive applications in the absorbent garment, or only in select applications as a construction adhesive for bonding parts of the garment as the top sheet, back sheet, absorbent core, and additional layer(s).

As the SAP material 286 and tow fibers 285 mix together to form central absorbent layer 284, which in turn is disposed between upper layer 280 and lower layer 282 at composite forming station 820, some of these SAP particles may become affixed in the adhesive 295 when the absorbent composite 28 is passed through the one or more nip rollers 821 at the core forming station 820. The composites 28 then are cut to length by cutting knife 830. Cutting knife 830 can be any suitable cutting device capable of cutting absorbent composite 28 of the invention. For example, cutting knife 830 can be comprised of a set of rollers; one being an anvil, and another having a knife attached at one point on the roller, whereby the diameter of the roller is selected to coordinate with the speed at which absorbent composites 28 are formed. The knife roller and anvil roller then can rotate at the same speed as the line speed to cut the absorbent composite 28 at select areas to form uniform length composites 28. Skilled artisans are capable of designing a suitable cutting knife 830 given the specifics of each article forming assembly line.

The absorbent composites 28 then are transported to garment forming station 800 via composite conveyor 880. Top sheet material 24 may be supplied to garment forming station 800 by top sheet supply mechanism 240, which can be any supply mechanism capable of supplying top sheet 24 to garment forming station 800. Preferably, top sheet material 24 is supplied via a supply roller 240 and select feed or guide rollers. Back sheet material 26 likewise can be supplied to garment forming station 800 by back sheet supply mechanism 260, which can be any supply mechanism capable of supplying back sheet 26 to garment forming station 800. Preferably, back sheet material 26 is supplied via a supply roller 260 and select feed or guide rollers. The garment forming station 800 brings together the respective components of absorbent article 10 by disposing the absorbent composite 28 between top sheet material 24, and back sheet material 26. The final absorbent article 10 then may be cut and folded to the appropriate size and shape downstream from forming station 800.

A feature of the present invention is that the absorbent composite 28 comprises a superabsorbent material having a Column Absorbency Under Load (CAUL) above 10 g/g at 0.3 psi, when subjected to the CAUL test described in detail below. It is preferred that the superabsorbent material 286 have a CAUL above 10.7 g/g, more preferably, greater than 11.5 g/g, and most preferably greater than about 12.6 g/g. Another feature of the present invention is that an absorbent garment contains an absorbent core that comprises such a superabsorbent material.

CAUL is a modified version of the Absorbency Under Load (AUL) test disclosed in U.S. Pat. No. 5,147,343, the disclosure of which is incorporated by reference herein in its entirety. AUL measures the ability of a superabsorbent material to swell under an applied force and thereby perform work. AUL is expressed as the amount (in milliliters) of an aqueous sodium chloride solution (0.9 weight percent sodium chloride) which the superabsorbent material can absorb per gram in one hour under a load of 21,000 dynes per square centimeter (approximately 0.3 psi). The AUL test requires a 2.54 cm inside diameter cylinder with a 100 mesh screen fused to the bottom of the cylinder. After the 0.16 gram layer of sample of superabsorbent material is placed in the cylinder, a 4.4 gram piston is inserted in the cylinder on top of the sample in order to apply the required pressure of 0.3 psi that is commonly experienced in infant diapers. The bottom of the screen then is exposed to the solution for one hour. The mass of the liquid absorbed by the superabsorbent material in grams is determined and the AUL is calculated by dividing the mass of the liquid absorbed by the mass of the superabsorbent material sample.

While this test is adequate for optimizing AUL in moderate superabsorbent material concentrations from approximately 30% to 45% where the superabsorbent material is homogeneously mixed in the absorbent core, it does not address the permeability of the superabsorbent material. In poorly homogenized absorbent composites, which can occur due to various circumstances such as improper mixing, too much settling, etc., and as the concentration of superabsorbent material in absorbent composites increases to above 45%, preferably from 50% to 95%, high permeability is desirable. It has not heretofore been known, however, that the combination of high AUL and high permeability are desirable features in a superabsorbent material. Although permeability can be tested separately in terms of free volume absorbency under load (FVAUL) or Saline Flow Conductivity (SFC), these tests do not measure the combination of AUL and permeability together. FVAUL is disclosed in Serial No. 09/685,608 entitled "Absorbent Articles Containing High FVAUL SAP," the disclosures f which is incorporated by reference herein in its entirety. Saline Flow Conductivity (SFC) is a measure of the ability of a material to transport saline fluid as disclosed in U.S. Pat. Nos. 5,562,646 and 6,232,520, the disclosures of which are incorporated by reference herein in their entirety.

The Column AUL test or CAUL provides a way to measure both AUL and permeability at the same time and thereby provide a mechanism of selecting and characterizing SAP materials that have superior performance in an absorbent composite with a high concentration of superabsorbent material as well as in an absorbent composite that has a layered superabsorbent material distribution. The CAUL test uses a larger sample size in order to provide a sample with a height that is approximately eight times higher than in the traditional AUL test. This increased height tests the permeability of the superabsorbent material in addition to AUL, thus allowing for optimization of these properties. Thus, the CAUL test described herein also accounts for gel blocking that may occur when the first layer of particles swell and prevent SAP particles further away from the fluid from contacting the fluid.

The invention now will be explained with reference to the following examples.

EXAMPLES

The following testing procedures were used to determine the CAUL values for a number of superabsorbent materials used in absorbent composites contained in absorbent garments.

Column Absorbency Under Load (CAUL) Test Procedure

Figure 5:
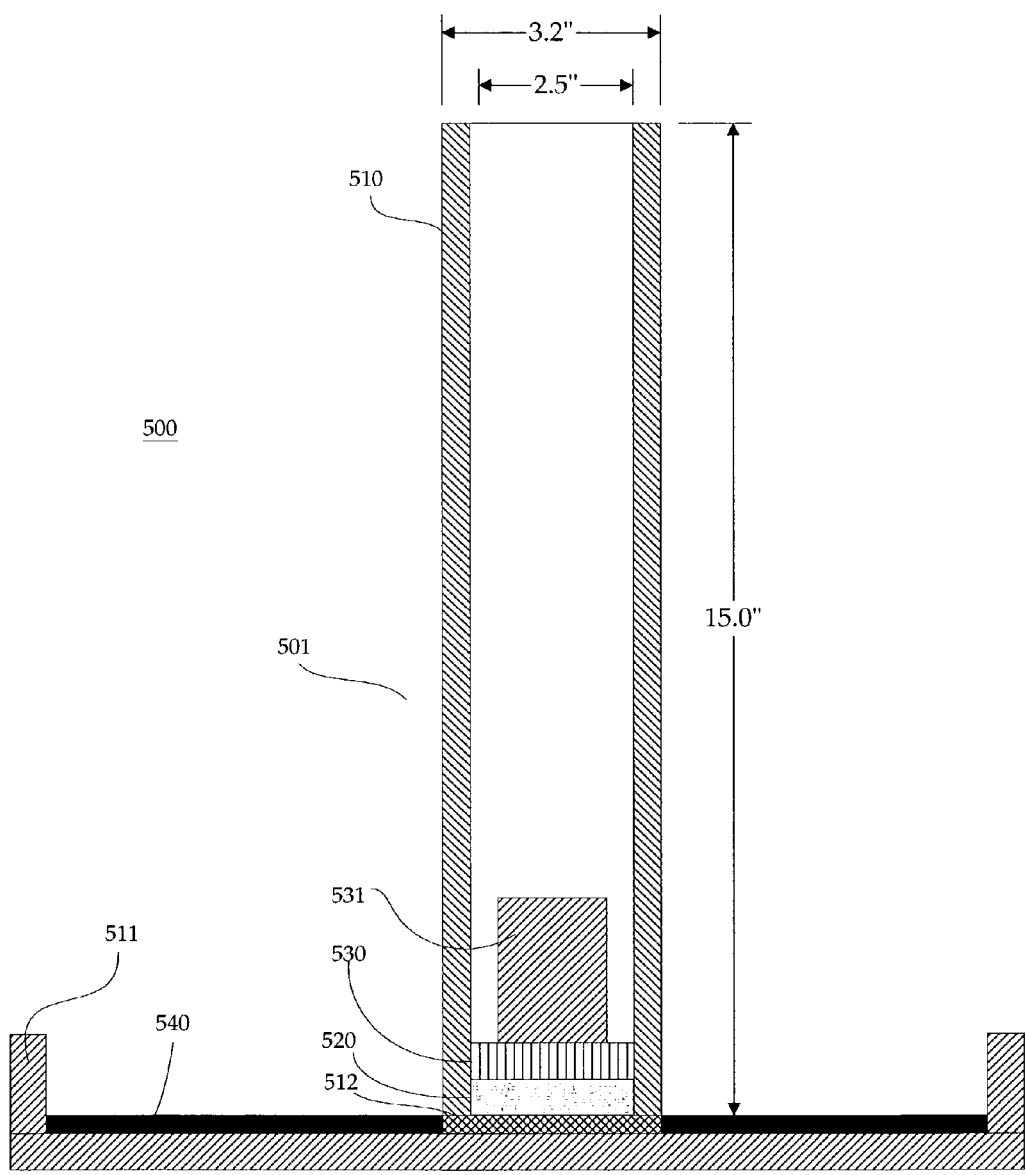
FIG. 5 is an illustration of an apparatus useful in carrying out the procedure for calculating column absorption under load (CAUL)

Sample Preparation: Samples for the CAUL test were prepared by rotating a sample container of superabsorbent material end over end several times in order to obtain a representative sample. If the superabsorbent material needed to be extracted from a diaper, it was carefully removed without contaminating the sample. The sample of superabsorbent material was then screened through a mesh of 300 to 600 microns. A 2 gram sample of the screened superabsorbent material 520 (FIG. 5) was then obtained and placed in a CAUL cylinder 510. The sample weight (SW) therefore was about 2 grams.

The CAUL cylinder 510 was made of Plexiglass with a stainless steel screen 512 fused to one end of the cylinder. The CAUL cylinder 510 had an inside diameter of 2.5 cm, an outside diameter of 3.2 cm and a height of 15 cm. The screen 512 was 36 microns (400 mesh). The superabsorbent material 520 was evenly distributed and did not cling to the sides of the cylinder 520 before starting the test. If static was present inside the cylinder, a magnetic cloth would be used to wipe the inside of the cylinder 510 before adding the sample 520. The sample was placed in the CAUL cylinder 510 and a cover plate 530 was placed into the CAUL cylinder 510 on top of the superabsorbent material 520. A piston 531 was then placed on top of the cover plate 530 and the assembly 501, including the cylinder 510, sample 520, cover plate 530 and piston 531, was weighed. This weight was recorded as the initial weight (IW).

Solution Preparation: Approximately 45 (g) of sodium chloride crystals were weighed in a dry weighing dish, and then added along with de-ionized water to a clean dry 5000 ml flask stopping at the 5000 ml mark. The concentration of the saline solution was measured with a refractometer to insure 0.9% concentration. About 10 drops of blue food coloring solution then was added to assist in viewing the solution during the test, and the solution was poured into a large beaker.

Test Method: A tray 511 for the CAUL test was filled with the 0.9% saline 540 so that the level was high enough to touch the bottom of the screen 512 when the assembly 501 was placed in the tray 511. The assembly 501 was placed in the tray 511 and a timer was started simultaneously. The assembly remained in the tray for 60 minutes. The level of the saline solution in the tray was maintained at a constant level during the 60 minutes so that the superabsorbent material could continuously absorb saline solution for the entire 60 minute period. After the timer stopped (after 60 minutes) the assembly 501 was removed from the tray 511 and weighed again. The weight was recorded as the final weight (FW). CAUL was calculated by subtracting the initial weight (IW) from the final weight (FW) and dividing the difference by the sample weight (SW), whereby the sample weight was 2 grams. (FW−IW)/SW.

Example 1

Figure 6:
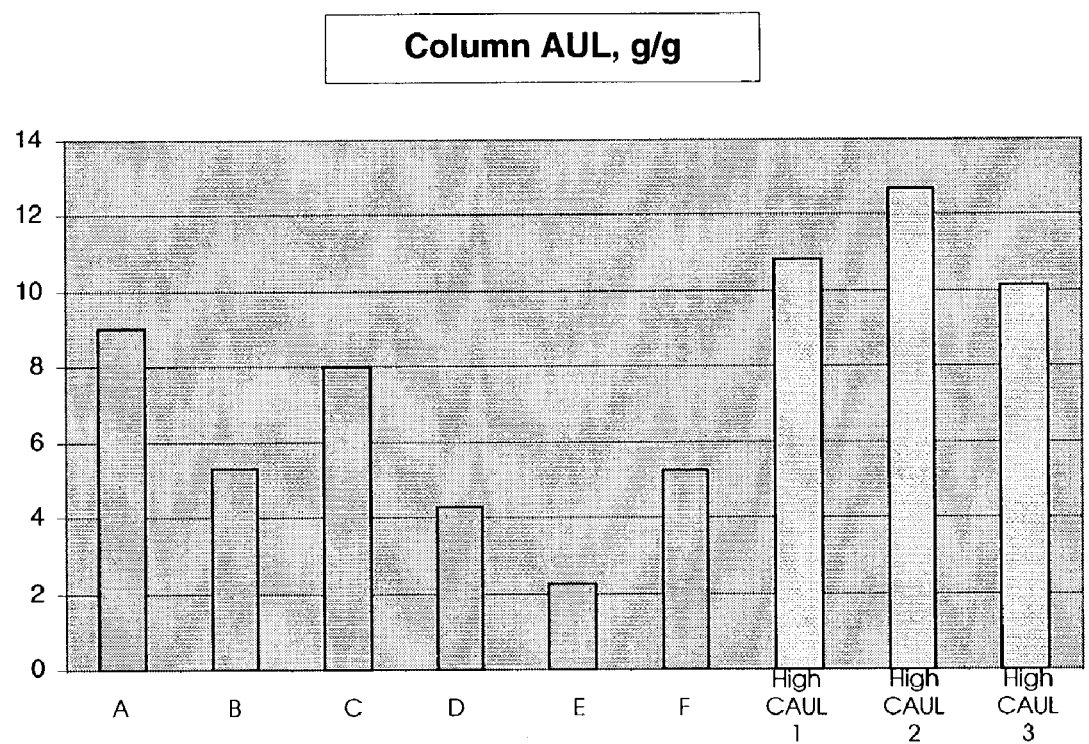
FIG. 6 is a graph showing column absorption under load (CAUL) for a number of superabsorbent polymers.

Samples A-L and High CAUL 1-3 were subjected to the CUAL test described above. Samples A and B were SAP samples extracted from commercially available absorbent garments: sample A being retrieved from a Luvs diaper, and sample B being retrieved from a Huggies Supreme diaper. Samples C-L were commercially available SAP. Sample C was BASF P-7710, set 1; Sample D was BASF P-7710, Lot #114EID; Sample E was Sumitomo Seika SA55Sx, Lot 3902125; Sample F was FASF E-1633; Sample G was BASF F-1610; Sample H was Nippon Shokubai PX3-W-1090; Sample I was BASF P-7200; Sample J was BASF P-7710 (set 1, P0116), Sample K was BASF E-1609; and Sample L was Stockhausen SP-1287. Samples High CAUL 1-3 were samples of an ultra high permeability SAP (UHI permeability B-3200) that were screened for various particle sizes. High CAUL 1 has a particle size of from 104 to 850 μm, High CAUL 2 had a particle size of from 100 to 300 μm, and High CAUL 3 had a particle size of from 600 to 1000 μm. Table 1 and FIG. 6 compare CAUL test values for commercially available absorbent materials, and samples High CAUL 1-3 that represent superabsorbent materials in accordance with the invention having CAUL values above 10 g/g.

TABLE 1

| Superabsorbent Material | Column AUL, g | Column AUL, g/g |
| --- | --- | --- |
| A | 18.0 | 9.0 |
| B | 10.6 | 5.3 |
| C | 16.1 | 8.0 |
| D | 18.3 | 9.13 |
| E | 8.6 | 4.3 |
| F | 4.6 | 2.3 |
| G | 10.5 | 5.2 |
| H | 3.19 | 1.6 |
| I | 11.2 | 5.6 |
| J | 14.5 | 7.25 |
| K | 11.6 | 5.8 |
| L | 7.2 | 3.6 |
| High CAUL 1 | 21.6 | 10.8 |
| High CAUL 2 | 25.4 | 12.7 |
| High CAUL 3 | 20.3 | 10.1 |

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. An absorbent article having a longitudinal dimension and a lateral dimension comprising:
   a top sheet;
   a back sheet; and
   an absorbent composite disposed between the top sheet and the back sheet,
   wherein the absorbent composite comprises a mixture of fibrous material and superabsorbent material; wherein the superabsorbent material has a Column Absorbency Under Load (CAUL) above about 10 g/g, and a particle size within the range of from about 100 μm to about 1,000 μm.

2. The absorbent article of claim 1, whereby the article has a first waist region, a second waist region longitudinally opposed to the first waist region, and a crotch region between the first and second waist regions, the article further comprising:
   at least one fastening element attached to a lateral edge of the first waist region; and
   one or more target devices attached to the article in the second waist region,
   where at least one fastening element and the one or more target devices are capable of attaching to one another, the one or more target devices being located so that the first waist region and second waist region of the garment may be joined to one another to secure the garment on a wearer.

3. The absorbent article of claim 2, further comprising elastic leg gathers comprising one or more elastic materials disposed adjacent a lateral edge of the crotch region, and standing leg gathers disposed on the top sheet adjacent the lateral edge of the crotch region.

4. The absorbent article of claim 2, wherein the at least one fastening element comprises a hook portion of a hook and loop fastener and the one or more target devices comprise the loop portion of a hook and loop fastener.

5. The absorbent article of claim 2, wherein the at least one fastening element is an adhesive tape and the one or more target devices comprise a tape receiving surface.

6. The absorbent article of claim 2, wherein the at least one fastening element is comprised of a pair of laterally extending tabs disposed on the lateral edges of the first waist region, whereby the laterally extending tabs each include at least one fastening element.

7. The absorbent article of claim 1, wherein at least one additional layer is disposed between the top sheet and the back sheet.

8. The absorbent article of claim 7, wherein the at least one additional layer is selected from the group consisting of a fluid acquisition layer, a distribution layer, an additional fibrous layer optionally containing SAP, a wicking layer, a storage layer, and combinations and fragments thereof.

9. The absorbent article of claim 1, wherein the absorbent composite comprises an upper layer, a lower layer, and a central absorbent layer disposed between the upper layer and lower layer; wherein the central absorbent layer comprises fibrous material and from about 50% to about 95% by weight of the super absorbent material.

10. The absorbent article of claim 9, wherein the fibrous material is at least one tow fiber selected from the group consisting of cellulose acetate fibers, polypropylene fibers, rayon fibers, LYOCELL fibers, polyacrylonitrile fibers, cotton fibers and cotton linter fibers.

11. The absorbent article of claim 9, wherein the central absorbent layer further comprises up to 10% by weight fluff wood pulp fibers.

12. The absorbent article of claim 1, wherein the fibrous material is a cellulose ester tow.

13. The absorbent article of claim 1, wherein the fibrous material is a polypropylene tow.

14. The absorbent article of claim 1, wherein the absorbent composite comprises an upper layer, a lower layer, and a central absorbent layer disposed between the upper layer and lower layer.

15. The absorbent article of claim 14, wherein the upper layer is fluid pervious, and the lower layer is fluid impervious.

16. The absorbent article of claim 14, wherein the upper layer and lower layer are comprised of the same material, and the material is selected from the group consisting of tissue, airlaid fluff pulp, synthetic non-woven material, and mixtures or combinations thereof.

17. The absorbent article of claim 1, wherein the superabsorbent material has a Column Absorbency Under Load (CAUL) above 10.7 g/g.

18. The absorbent article of claim 1, wherein the superabsorbent material has a Column Absorbency Under Load (CAUL) above 11.5 g/g.

19. The absorbent article of claim 1, wherein the superabsorbent material has a Column Absorbency Under Load (CAUL) above 12.6 g/g.

20. An absorbent composite comprising a mixture of fibrous material and superabsorbent material; wherein the superabsorbent material has a CAUL above 10 g/g, and a particle size within the range of from about 100 μm to about 1,000 μm.

21. The absorbent composite of claim 20, wherein the superabsorbent material has a CAUL above 10.7 g/g.

22. The absorbent composite of claim 20, wherein the superabsorbent material has a CAUL above 11.5 g/g.

23. The absorbent composite of claim 20, wherein the superabsorbent material has a CAUL above 12.6 g/g.

24. The absorbent composite of claim 20, wherein the absorbent composite comprises an upper layer, a lower layer, and a central absorbent layer comprising the mixture of fibrous material and superabsorbent material disposed between the upper layer and lower layer.

25. The absorbent composite of claim 21, wherein the central absorbent layer comprises from about 50% to about 95% by weight superabsorbent material.

26. A method of making an absorbent composite comprising preparing a mixture of fibrous material and superabsorbent material; wherein the superabsorbent material has a CAUL above 10 g/g, and a particle size within the range of from about 100 μm to about 1,000 μm.

27. The method of claim 26, wherein the superabsorbent material has a CAUL above 10.7 g/g.

28. The method of claim 26, wherein the superabsorbent material has a CAUL above 11.5 g/g.

29. The method of claim 26, wherein the superabsorbent material has a CAUL above 12.6 g/g.

30. The method of claim 26, further comprising:
 b) preparing an upper layer and a lower layer; and
 c) disposing the absorbent composite between the upper layer and lower layer.

31. A method of making an absorbent article comprising:
 a) preparing a top sheet and a back sheet;
 b) preparing an absorbent composite by:
  b1) preparing a mixture of fibrous material and superabsorbent material;
 wherein the superabsorbent material has a CAUL above 10 g/g, and a particle size within the range of from about 100 μm to about 1,000 μm; and
 c) disposing the absorbent composite between the top sheet and the back sheet to form an absorbent article.

32. The method of claim 31, wherein preparing the absorbent composite further comprises:
 b2) preparing a lower layer and an upper layer; and
 b3) disposing the absorbent composite is between the upper layer and lower layer.

33. The method of claim 31, wherein the absorbent composite comprises from about 50% to about 95% by weight super absorbent material.

34. The method of claim 31, wherein the fibrous material of the absorbent composite comprises at least one tow fiber selected from the group consisting of cellulose acetate fibers, polypropylene fibers, rayon fibers, LYOCELL fibers, polyacrylonitrile fibers, cotton fibers and cotton linter fibers.

35. The method of claim 31, wherein the absorbent composite further comprises up to 10% by weight fluff wood pulp fibers.

36. The method of claim 31, wherein the fibrous material is a cellulose ester tow.

37. The method of claim 31, wherein the fibrous material is a polypropylene tow.

38. A superabsorbent material having a CAUL above 10 g/g, and a particle size within the range of from about 100 μm to about 1,000 μm.

39. The superabsorbent material of claim 38, wherein the superabsorbent material has a CAUL above 10.7 g/g.

40. The superabsorbent material of claim 38, wherein the superabsorbent material has a CAUL above 11.5 g/g.

41. The superabsorbent material of claim 38, wherein the superabsorbent material has a CAUL above 12.6 g/g.

* * * * *